(12) United States Patent
Johnston et al.

(10) Patent No.: US 10,126,300 B2
(45) Date of Patent: Nov. 13, 2018

(54) IMMUNOSIGNATURE BASED DIAGNOSIS AND CHARACTERIZATION OF CANINE LYMPHOMA

(71) Applicants: Stephen Johnston, Tempe, AZ (US); Joseph Legutki, Tempe, AZ (US); Douglas Thamm, Fort Collins, CO (US)

(72) Inventors: Stephen Johnston, Tempe, AZ (US); Joseph Legutki, Tempe, AZ (US); Douglas Thamm, Fort Collins, CO (US)

(73) Assignees: Arizona Board of Regents of behalf of Arizona State University, Scottsdale, AZ (US); Colorado State University Research Foundation, Fort Collins, CO (US)

( * ) Notice: Subject to any disclaimer, the term of this patent is extended or adjusted under 35 U.S.C. 154(b) by 137 days.

(21) Appl. No.: 15/104,503

(22) PCT Filed: Dec. 16, 2014

(86) PCT No.: PCT/US2014/070509
§ 371 (c)(1),
(2) Date: Jun. 14, 2016

(87) PCT Pub. No.: WO2015/095136
PCT Pub. Date: Jun. 25, 2015

(65) Prior Publication Data
US 2016/0320392 A1 Nov. 3, 2016

Related U.S. Application Data

(60) Provisional application No. 61/917,203, filed on Dec. 17, 2013.

(51) Int. Cl.
G01N 33/574 (2006.01)
C40B 40/10 (2006.01)
C07K 4/12 (2006.01)

(52) U.S. Cl.
CPC ....... *G01N 33/57407* (2013.01); *C40B 40/10* (2013.01); *G01N 33/57484* (2013.01)

(58) Field of Classification Search
CPC ........ G01N 33/57407; G01N 33/57484; C40B 40/10
See application file for complete search history.

(56) References Cited

U.S. PATENT DOCUMENTS

2002/0160373 A1  10/2002  Avery et al.
2007/0003954 A1*  1/2007  Kodadek .......... G01N 33/54366
                                                          435/6.14

(Continued)

OTHER PUBLICATIONS

Siegel et al., Cancer Statistics, 2013., CA: A Cancer Journal for Clinicians, Jan. 2013, 63(1):11-30.

(Continued)

*Primary Examiner* — Jeremy C Flinders
(74) *Attorney, Agent, or Firm* — Gavin J. Milczarek-Desai; Quarles & Brady LLP

(57) ABSTRACT

Methods for diagnosing and characterizing lymphoma, as well as evaluating the disease-free interval following treatment, utilizing patient antibodies bound to peptide microarrays in comparison to an immunosignature characteristic of a lymphoma state or a non-lymphoma state. Characterization includes subtyping of lymphoma utilizing an immunosignature characteristic of a B-cell or T-cell lymphoma.

6 Claims, 6 Drawing Sheets

(56) References Cited

U.S. PATENT DOCUMENTS

| | | |
|---|---|---|
| 2012/0003744 A1 | 1/2012 | Mian et al. |
| 2012/0021983 A1 | 1/2012 | Tsichlis et al. |
| 2013/0079424 A1 | 3/2013 | Gerber et al. |

OTHER PUBLICATIONS

Shankland et al., Non-Hodgkin lymphoma., Lancet, Sep. 2012, 380(9844):848-57.

Evans et al., Non-Hodgkin lymphoma., Lancet, Jul. 2003, 362(9378):139-46.

Larouche et al., Lymphoma Recurrence 5 Years or Later Following Diffuse Large B-Cell Lymphoma: Clinical Characteristics and Outcome., Journal of Clinical Oncology, Apr. 2010, 28(12):2094-100.

Marconato et al., The dog as a possible animal model for human non-Hodgkin lymphoma: a review., Hematologica Oncology, 2013, 31(1):1-9.

Vail et al., Hematopoietic tumors., Small Animal Clinical Oncology (4th ed., 2007, eds. Withrow and Vail), 2007, 699-784.

Hori et al., Mathematical model identifies blood biomarker-based early cancer detection strategies and limitations., Science Translation Medicine, Nov. 2011, 3(109):109ra116(1-19).

Hu et al., Identification of autoantibody biomarkers for primary Sjogren's syndrome using protein microarrays., Proteomics, Apr. 2011, 11(8):1499-507.

Mou et al., Immunoproteomics to identify tumor-associated antigens eliciting humoral response., Cancer Letters, Jun. 2009, 278(2):123-9.

Stafford et al., Physical Characterization of the "Immunosignaturing Effect.," Molecular & Cellular Proteomics, Apr. 2012, 11(4):M111. 011593(14 pages).

AF Geijersstam et al., Stability over Time of Serum Antibody Levels to Human Papillomavirus Type 16., Journal of Infectious Diseases, 1998, 177(6):1710-4.

Chase et al., Evaluation of Biological Sample Preparation for Immunosignature Based Diagnostics., Clinical and Vaccine Immunology, 2012, 19(3):352-8.

Sykes et al., Immunosignaturing: a critical review. Trends in Biotechnology, Jan. 2013, 31(1):45-51.

Restrepo et al., Feasibility of an early Alzheimer's disease immunosignature diagnostic test., Journal of Neuroimmunology, Jan. 2013, 254(1-2):154-60.

Hughes et al., Immunosignaturing Can Detect Products from Molecular Markers in Brain Cancer., PLoS One, Jul. 2012, 7(7):e40201(7 pages).

Johnson et al., Adjusting batch effects in microarray expression data using empirical Bayes methods., Biostatistics, 2007, 8(1):118-27.

Meyer et al., Package e1071: Misc Functions of the Department of Statistics, R package version 1.6-T, Tu Wien, 2015.

Starrak et al., Correlation between thoracic radiographic changes and remission/survival duration in 270 dogs with lymphosarcoma., Veterinary Radiology & Ultrasound, 1997, 38(6):411-8.

Regan et al., Diagnostic evaluation and treatment recommendations for dogs with substage-a high-grade multicentric lymphoma: results of a survey of veterinarians., Veterinary and Comparative Oncology, 2012, 11(4):287-95.

Planinc-Peraica et al., Serum immunoglobulins in non-Hodgkin's lymphoma patients., Collegium Antropologicum, 2010, 34(2):407-11.

Biggar et al., Immunoglobulin subclass levels in patients with non-Hodgkin lymphoma., International Journal of Cancer, 2009, 124(11):2616-20.

Yamashita et al., XCR1 Expression and Biased VH Gene Usage Are Distinct Features of Diffuse Large B-Cell Lymphoma Initially Manifesting in the Bone Marrow., American Journal of Clinical Pathology, 2011, 135(4):556-64.

Warsame et al., Splenic marginal zone lymphoma with VH1-02 gene rearrangement expresses poly- and self-reactive antibodies with similar reactivity., Blood, 2011, 118(12):3331-9.

Perez et al., Primary cutaneous B-cell lymphoma is associated with somatically hypermutated immunoglobulin variable genes and frequent use of VH1-69 and VH4-59 segments., British Journal of Dermatology, 2010, 162(3):611-8.

Hashimoto et al., Superantigens and autoantigens may be involved in the pathogenesis of gastric mucosa-associated lymphoid tissue lymphoma., International Journal of Hematology, Aug. 2001, 74(2):197-204.

Deeb et al., Super-SILAC allows classification of diffuse large B-cell lymphoma subtypes by their protein expression profiles., Molecular & Cellular Proteomics, May 2012, 11(5):77-89.

Stranneheim et al., A comparison between protein profiles of B cell subpopulations and mantle cell lymphoma mils., Proteome Science, 2009, 7:43(8 pages).

Felsburg, Overview of immune system development in the dog: comparison with humans., Human & Experimental Toxicology, 2002, 21(9-10):487-92.

Manz et al., Maintenance of serum antibody levels., Annual Review of Immunology, 2005, 23:367-86.

Mumtaz et al., Bone marrow of NZB/W mice is the major site for plasma cells resistant to dexamethasone and cyclophosphamide: Implications for the treatment of autoimmunity., Sep. 2012, 39(3):180-8.

Dilillo et al., Maintenance of Long-Lived Plasma Cells and Serological Memory Despite Mature and Memory B Cell Depletion during CD20 Immunotherapy in Mice., Journal of Immunology, Jan. 2008, 180(1):361-71.

Sato et al., The prognostic significance of minimal residual disease in the early phases of chemotherapy in dogs with high-grade B-cell lymphoma, Veterinary Journal, Mar. 2013, 195(3):319-24.

Elliott et al., Thymidine kinase assay in canine lymphoma., Veterinary and Comparative Oncology, Mar. 2013, 11(1):1-13.

Ratcliffe et al., Proteomic identification and profiling of canine lymphoma patients., Veterinary and Comparative Oncology, Jun. 2009, 7(2):92-105.

Johnston et al., Immunosignature Based Test for the Diagnosis and Characterization of Canine Lymphoma., AzTE disclosure, 2016, <http://azte.technologypublisher.com/technology/22691#>.

Yang et al., Segmentation and intensity estimation for microarray images with saturated pixels., BMC Bioinformatics, 2011, 12:462(10 pages).

Legutki et al., Immunosignatures can predict vaccine efficacy., PNAS, Nov. 2013, 110(46):18614-9.

Siedlecki et al., Evaluation of an actinomycin-D-containing combination chemotherapy protocol with extended maintenance therapy for canine lymphoma., Canadian Veterinary Journal, Jan. 2006, 47(1):52-9.

Richards et al., Gene profiling of canine B-cell lymphoma reveals germinal center and postgerminal center subtypes with different survival times, modeling human DLBCL., Cancer Research, Aug. 2013, 73(16):5029-39.

Johnston et al., The immunosignature of canine lymphoma: characterization and diagnostic application., BMC Cancer, 2014, 14:657(11 pages).

International Search Report, Patent Cooperation Treaty, PCT/US14/70509, dated Apr. 30, 2015.

* cited by examiner

IMMUNOSIGNATURE BASED DIAGNOSIS AND CHARACTERIZATION OF CANINE LYMPHOMA

CROSS-REFERENCE TO RELATED APPLICATIONS

This application is a 371 application of PCT/US2014/070509 filed Dec. 16, 2014, which is based on, claims a priority benefit from, and incorporates herein by reference, U.S. Provisional Patent Application No. 61/917,203, filed Dec. 17, 2013, and entitled "Immunosignature Based Diagnosis and Characterization of Canine Lymphoma."

FIELD OF THE INVENTION

Embodiments disclosed herein relate to the field of veterinary medicine and more particularly to materials and methods useful in the non-invasive diagnosis and characterization of canine lymphoma.

BACKGROUND OF THE INVENTION

Clinical diagnosis of cancer is a complex process usually initiated by presentation of indicative symptoms. Suspected conditions are identified as possible differential diagnosis and a battery of blood tests, urinalysis, imaging tests, and biopsy are conducted before final diagnosis is made. Biomarkers have been identified for some cancers, but have limited use as a primary screening tool.

Non-Hodgkin's lymphoma (NHL) is a spontaneously occurring neoplasm of particular interest. NHL newly affects 69,740 people annually in the United States (1) and has had a steadily increasing incidence in the United States and Europe (2). If diagnosed early, effective treatments can be selected (2, 3) and the 5 year survival is 72% (1). However, diagnosis is complicated by the lack of a non-invasive test and is presently made by clinical signs, physical examination findings and imaging, with confirmation of disease by biopsy.

Even with effective treatment, 50% of patients with aggressive lymphomas have residual disease and eventually relapse (4). Lymphoma is one of the most commonly encountered canine neoplasms, generally affecting middle-aged to older dogs. Breeds reported to be at increased risk include boxers, bull mastiffs, Bassett hounds, Saint Bernards, Scottish terriers, Airedales, golden retrievers and English bulldogs (6). Typically dogs present with an aggressive high-grade multicenteric lymphoma, of which diffuse large B-cell lymphoma (DLBCL) is the most common subtype (5). Following chemotherapy, 95% all dogs relapse following a period of remission.

While approximately 85% of dogs present with multi-centric peripheral lymphadenopathy, a small percentage present with visceral disease only (e.g. primary mediastinal, gastrointestinal or hepatosplenic forms), which requires serial imaging in order to monitor remission status. In humans, remission status is monitored by CT, MRI or PET scans (2). Facile and early detection of relapse may facilitate re-induction of remission and improve outcome.

SUMMARY OF THE INVENTION

This disclosure relates to the application of immunosignature methods to diagnosis and characterization of canine lymphoma. A single blood test capable of diagnosing cancer with high sensitivity and specificity would enhance patient care by streamlining the diagnostic process. A serological test for monitoring lymphoma would have utility at multiple stages: early detection, diagnosis and monitoring of residual disease.

Spontaneous canine lymphoma and human NHL have nearly identical presentations and pathologies, making them ideal partner species in which to explore blood based diagnostics. A serological test would facilitate routine monitoring during an annual wellness examination, enable faster diagnosis when lymphoma is suspected and allow monitoring of lymphoma following treatment. Design of such a test for lymphoma is dependent on the identification of an appropriate biomarker.

Ideally, this test would be applicable to early disease, but to do so it must overcome the "blood dilution" problem: that is, if $10^6$ initiating cancer cells release 1000 molecules each of a biomarker into two liters of blood at steady state, the concentration of this biomarker would only be $1.3 \times 10^{-14}$ M), placing it below the detection limits of even the best assays.

Antibodies are an ideal solution to this problem. Self-reactive antibodies have been reported in cancers and autoimmune disease. Arising early in the course of a disease, the activation of a single B cell results in an $\sim 10^{11}$ amplification of signal in only a week. Furthermore, antibodies are stable in blood, enabling archived samples to be used in assay development or serial monitoring.

In view of the above, a new technology termed immunosignaturing has been developed which displays the circulating antibody repertoire upon an addressable, machine readable random peptide microarray. The random sequences allow an unbiased display of all types of antibody binding. The peptides on the microarray serve as mimetics of the actual epitopes and capitalize on the cross-reactivity of antibodies. Even if the actual epitope is not present, another peptide that the same antibody can bind will be present. In addition, the arrays are inexpensive and can be adapted to high throughput sample processing.

In embodiments disclosed herein, the immunosignature is used to characterize the humoral response to canine lymphoma and demonstrate its clinical utility in diagnosing different subtypes of disease. Pretreatment serum samples from patients presenting with T cell and B cell LSA are compared to healthy dogs. Serial serum samples from patients that experienced remission following chemotherapy and ultimately relapsed are also disclosed. Immunosignatures informative for each subtype of disease and their diagnostic efficacy are reported.

BRIEF DESCRIPTION OF THE FIGURES

Some of the figures are meant to be presented in color. Therefore, where color is indicated below, "red" generally corresponds to the darkest squares in the black-and-white reproductions provided herewith and represents 5 fold greater than the per peptide median normalized intensity; "yellow" generally corresponds to the lightest squares and represents the median; and "blue" generally corresponds to squares that are between the darkest and lightest squares and represents 5 fold below the median.

DETAILED DESCRIPTION OF THE PREFERRED EMBODIMENTS

Figure 1:
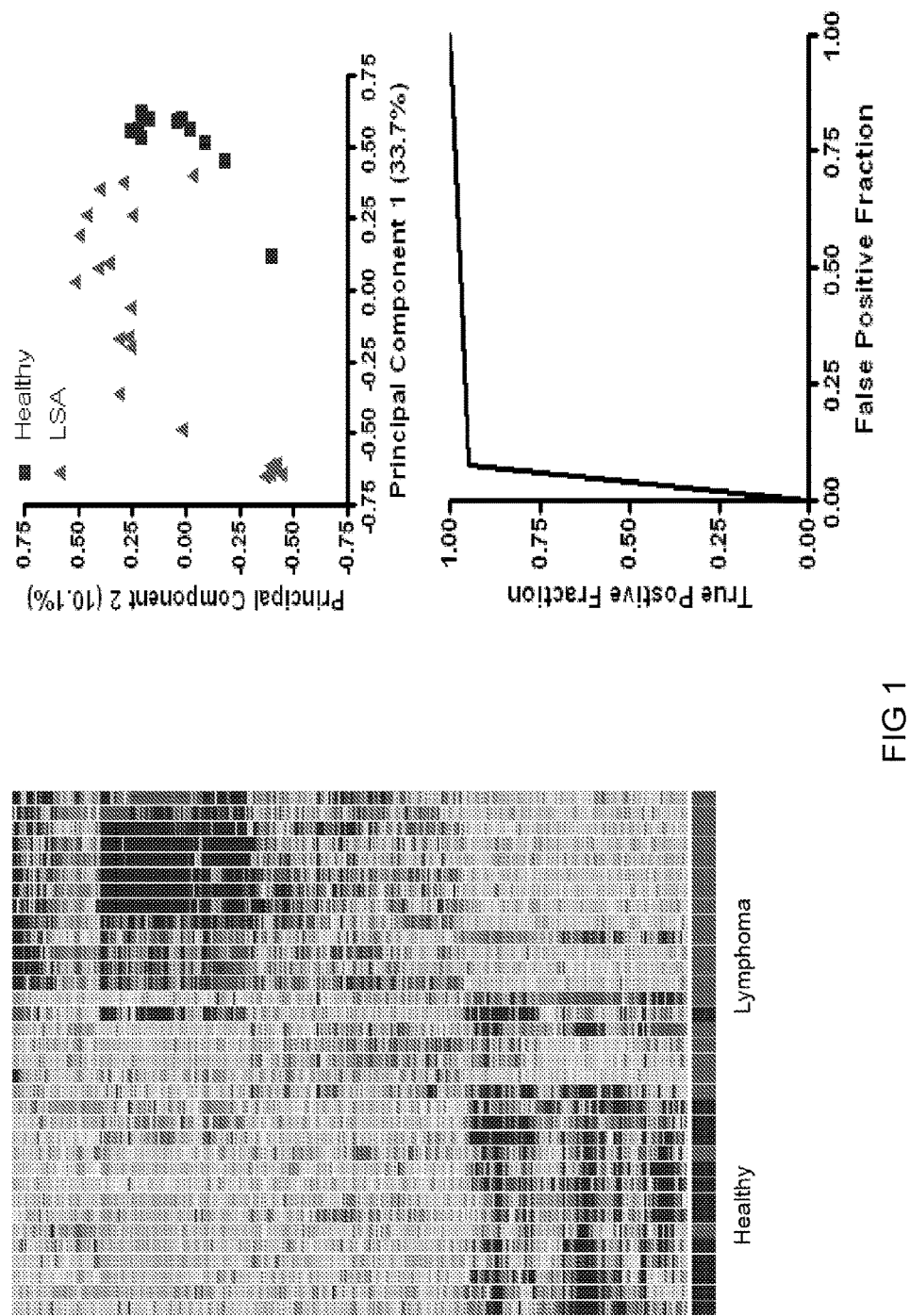
FIG. 1. The immunosignature distinguishes lymphoma patients from healthy dogs. A Student's T-test ($p<0.05$ with FDR) and a 1.5 fold change between classes was used to select 340 informative peptides. The distribution of intensities is shown in the Heatmap (A). Colors represent the per peptide median normalized intensities. Yellow indicates the median, Red five fold above the median and Blue 0.25 fold below the median. Each row represents a peptide and each column represents and individual. Individuals were clustered in GeneSpring using the Pearson correlation to each other. Variation among individuals based on the 340 peptides is shown in the PCA plot (B) where the first two principal components are plotted. The classification efficacy is plotted in the ROC curve in (C). Print run one and the KPL congugate was used for this assay.

The following abbreviations are used throughout this disclosure:
LSA B or T cell Lymphoma
LSA-B B cell Lymphoma
LSA-T T cell Lymphoma
DFI Disease Free Interval
SVM Support Vector Machine
LOOCV Leave One Out Cross Validation
FDR The Benjamani and Hochberg False Discovery Rate Correction To evaluate the immunosignature as a diagnostic for spontaneous canine lymphoma at both initial diagnosis and evaluating the disease-free interval following treatment, the following experiments were performed. However, these experiments are merely examples and not meant to limit the claims in any way.

Experimental Design, Results, and Conclusions in Outline: Serum from dogs with confirmed lymphoma (B cell n=38, T cell n=11) and clinically normal dogs (n=39) were analyzed. Serum antibody responses were characterized by analyzing the binding pattern, or immunosignature, of serum antibodies on a non-natural sequence peptide microarray.

Peptides were selected and tested for the ability to distinguish healthy dogs from those with lymphoma and to distinguish lymphoma subtypes based on immunophenotype. The immunosignature of dogs with lymphoma were evaluated for individual signatures. Changes in the immunosignatures were evaluated following treatment and eventual relapse.

Results: Despite being a clonal disease, both an individual immunosignature and a generalized lymphoma immunosignature were observed in each dog. The general lymphoma immunosignature identified in the initial set of dogs (n=32) was able to predict health status in an independent set of dogs (n=42, 97% accuracy). A separate immunosignature was able to distinguish the lymphoma based on immunophenotype (n=25, 88% accuracy). The individual immunosignature was capable of confirming remission three months following diagnosis Immunosignature at diagnosis was able to predict which dogs with B cell lymphoma were going to relapse in less than 120 days (n=33, 97% accuracy).

Conclusion: The immunosignature can serve as a multilevel diagnostic for canine, and potentially human lymphoma.

Detailed Experiments: Materials and Methods—Patient Sera. Serum samples were obtained from clinically normal client-owned dogs or dogs with histologically or cytologically confirmed LSA and stored at −80° C. from the time of presentation, prior to any specific therapy, and were collected with owner consent and approval of the CSU Institutional Animal Care and Use Committee (Protocol #10-2007A). In a subset of patients, sera were collected serially from dogs with LSA at each subsequent recheck visit, up to and including the time of relapse.

Peptide Microarrays. The CIM10Kv2 random peptide microarrays used for immunosignaturing have been described previously. These microarrays contain 10,000 random peptides containing 17 random residues and an N-terminal CSG linker. Known peptide sequences were piezo-electrically printed in an addressable format with two printings of the 10,000 peptides per standard slide. Arrays were obtained from the Peptide Array Core at Arizona State University (peptidearraycore.com). Two print runs having a quality control technical cross batch correlation of 0.67 were used for this study.

Binding Sera to the Immunosignature Arrays. Patient serum was used to probe the CIM10Kv2 immunosignaturing microarray as described previously using a Tecan HS4800. Prior to the assay, unbound peptide was removed by prewashing the arrays in 7.33% acetonitrile, 30% isopropanol and 0.5% trifluoroacetic acid. The arrays were then blocked in phosphate buffered saline with 0.05% Tween 20 (PBST), 3% Bovine Serum Albumin (BSA) and 0.014% mercaptohexanol for 1 hour. Following washing with PBST, serum was diluted to 1:500 in incubation buffer (PBST with 3% BSA) for 1 hour at 37° C. Bound IgG was then detected using 5.0 nM anti-dog IgG (Fc gamma specific)-Dylight 649 for 1 hour. Anti-Dog IgG (gamma) from KPL was used in the first batch of arrays and Anti-Dog IgG (gamma) from Jackson Immuno Research was used in the second batch due to discontinuation of the KPL conjugate. The microarrays were then washed in PBST then distilled water. Nitrogen dried slides were then scanned at 633 nm using an Agilent 'C' type scanner at 100% laser power and 100% PMT.

Statistical Analysis. Raw array images were aligned using GenePix (Molecular Devices) to produce a tab deliminated results file. Artifacts were removed by flagging the features as bad. Results files were evaluated in GeneSpring (Agilent) or Bioconductor R (2.15.2). For all analysis, the arrays run with the KPL and the Jackson Immuno Research conjugates were treated separately. The ComBat algorithm was used to minimize assay batch effects on per chip median normalized scores. Criteria for selecting informative peptides between classes were a Student's T-test p value less than 0.05 with the Benjamani and Hochberg False Discovery Rate (FDR) correction and a minimum fold change of 1.5× between class averages.

A support vector machine in R (e1071 library) (17) was used for classification with the following settings type=C, Kernel=polynomial, degree=1, gamma=default. Iterative testing was done in R by splitting the patient population into 75% training for peptide selection and the remaining 25% into test sets to evaluate classification based on the selected peptides. Heatmaps were generated in GeneSpring with individuals and peptides clustered using the default Pearson correlation settings. Principal component values were obtained in GeneSpring and plotted in GraphPad Prism. Power analysis conducted in R at 80% power, $5.0 \times 10^{-6}$ significance level (FDR adjusted p value), Standard deviation of 50%, and a 1.5 fold change (delta) between groups indicated a minimum of 11 samples were needed for each comparison made. All comparisons were adequately powered.

Results: The Study Plan. The diagnosis and treatment of many cancers, including canine and human lymphoma, is complicated by the lack of a non-invasive serological test. Having demonstrated that the immunosignature is capable of simultaneously classifying cancers including multiple subtypes of brain cancer, we hypothesized the immunosignature could be applicable to canine lymphoma. The CSU tumor archive was canvassed to select 38 B cell LSA, 11 T cell LSA and 39 clinically healthy dogs collected as part of ongoing prospective archiving efforts Summary statistics of age, breed and clinical presentation are presented in Table 1.

The Immunosignature Distinguishes Canine Lymphoma Patients from Healthy Dogs. Initially, the immunosignature was evaluated with a small set of dogs to determine the ability to distinguish LSA (either B or T cell) from healthy. Patient (n=21) and healthy dog (n=11) sera were randomized and applied to the CIM10Kv2 array. Per chip median normalized values were ComBat normalized to remove batch effects and then compared between LSA and healthy dogs.

A Student's T-test selected 340 peptides having an FDR corrected p value less than 0.05 and a minimum 1.5 fold difference in intensity between classes. Reactivity is shown in the heatmap in FIG. 1A. Separation of healthy and LSA is shown in the PCA in FIG. 1B. Leave one out cross validation (LOOCV) was able to separate LSA and healthy with 94% accuracy. A ROC curve is shown in FIG. 1C. A similar distinction was made using the CIM10Kv1 arrays (data not shown). This demonstrates that the immunosignature can distinguish canine lymphoma patients from healthy dogs.

The Immunosignature Predicts Health Status in an Independent Set of Dogs. To test the predictive ability of the peptides identified above, additional B cell LSA patients (n=20) and healthy donors (n=22) were obtained. Serum from all B cell LSA patients (n=38) and healthy donors (n=39) were randomized and used to probe the CIM10Kv2. Technical requirements necessitated that serum from all dogs be run on a second print run of the CIM10Kv2 and detected using a different secondary antibody due to product discontinuation by the original supplier.

Figure 2:
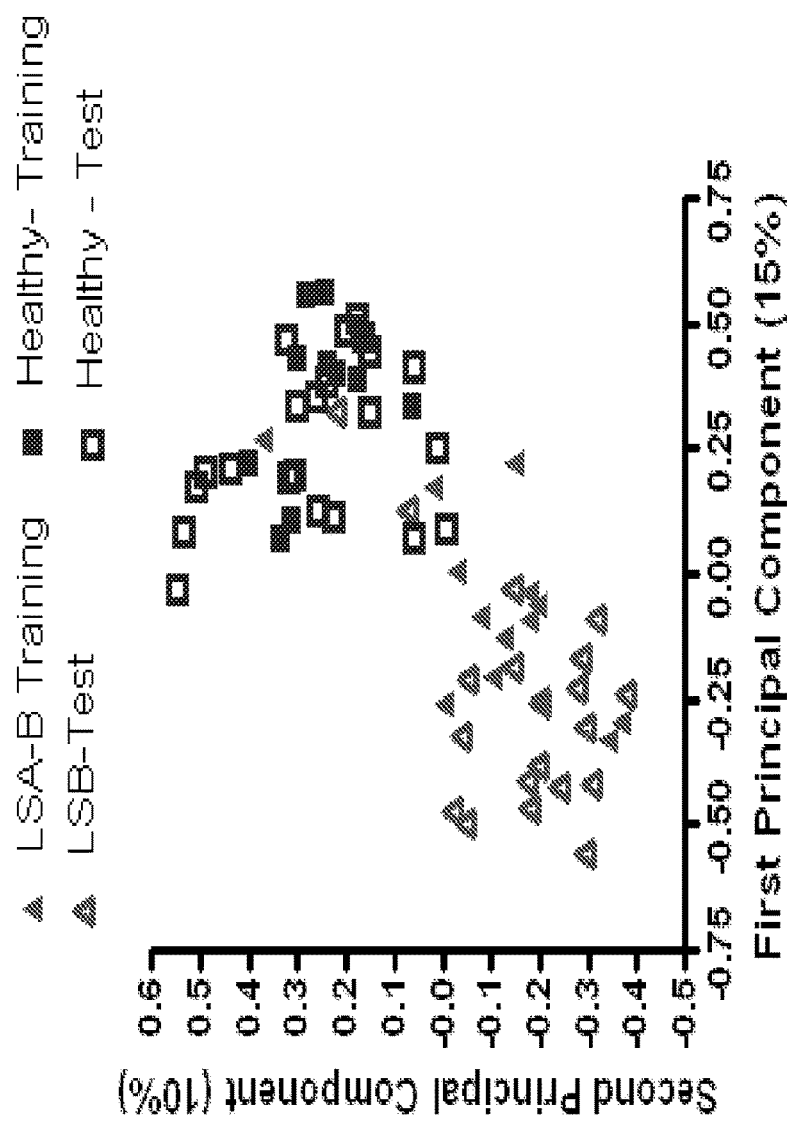
FIG. 2. Classification of an independent test set into LSA patients and healthy dogs. The 340 peptides identified as informative between LSA and healthy dogs (p<0.05 with FDR and greater than 1.5 fold difference between classes) were used to train a support vector machine and predict a test set of dogs. The variance of all dogs in both the training set (solid symbols) and test set (open symbols) are presented in a principal component analysis. The first two principal components are presented as the x and y scalar values and each symbol represents the replicate average for a single dog. Peptides were selected on the training set using the KPL conjugate. The Jackson conjugate was used for both the training and test set in this assay.

The 340 peptides selected above to separate LSA and healthy clearly separated the expanded test set of dogs, even though the print run and anti-IgG secondary antibody were different (FIG. 2). When the training set arrays from print run 1 were used to predict the test set from print run 2, the accuracy was 97%: one LSA-B patient was miscalled as healthy. This accuracy was the same whether the training set arrays were from the same or different batch than the test set.

To exclude the possibility that the distinction between LSA and healthy was an artifact of this division of training and test sets, the dogs were iteratively randomized into training (75%) and test (25%) sets. The training set was used to select peptides having a p value <0.05 with FDR and a minimum fold change between classes of 1.5 fold. The peptides were then used to train an SVM and predict class membership of the test set. Over 10,000 randomizations into training and test sets, the median performance on the test set accuracy was 88.2%, sensitivity was 88.9% and specificity was 87% (Table 2).

To assess the how much of the immunosignature is due to other factors, all healthy and B cell lymphoma dogs were combined and divided based on gender and age. Separation of dogs into two classes based on age (division was 7 years old) yielded 14 significant peptides that were unable to classify the dogs on either a PCA or SVM. Further separation into male and female dogs yielded one significant peptide that was unable to classify in either a PCA or SVM. This suggests that the difference in immunosignature based on health or disease is due to the lymphoma not another factor. Taken together, this demonstrates that the immunosignature is both capable of predicting an independent test set and is stable across array print runs and detection systems.

The Immunosignature Can Distinguish Dogs with T cell Lymphoma from Those with B cell Lymphoma. In dogs, T-cell LSA tends to be a more aggressive form of lymphoma than B-cell LSA and determining this distinction can have impacts on both outcome and, in some cases, choice of treatment. For this reason, immunophenotyping is commonly performed as part of initial staging in dogs with LSA. The immunosignature of the B cell LSA (n=14) and T cell LSA (n=11) patients were compared using a Student's T-test and 47 peptides had a p value less than 0.05 with FDR and a minimum 1.5 fold difference between classes. Reactivity is shown in the heatmap in FIG. 3A.

Figure 3:
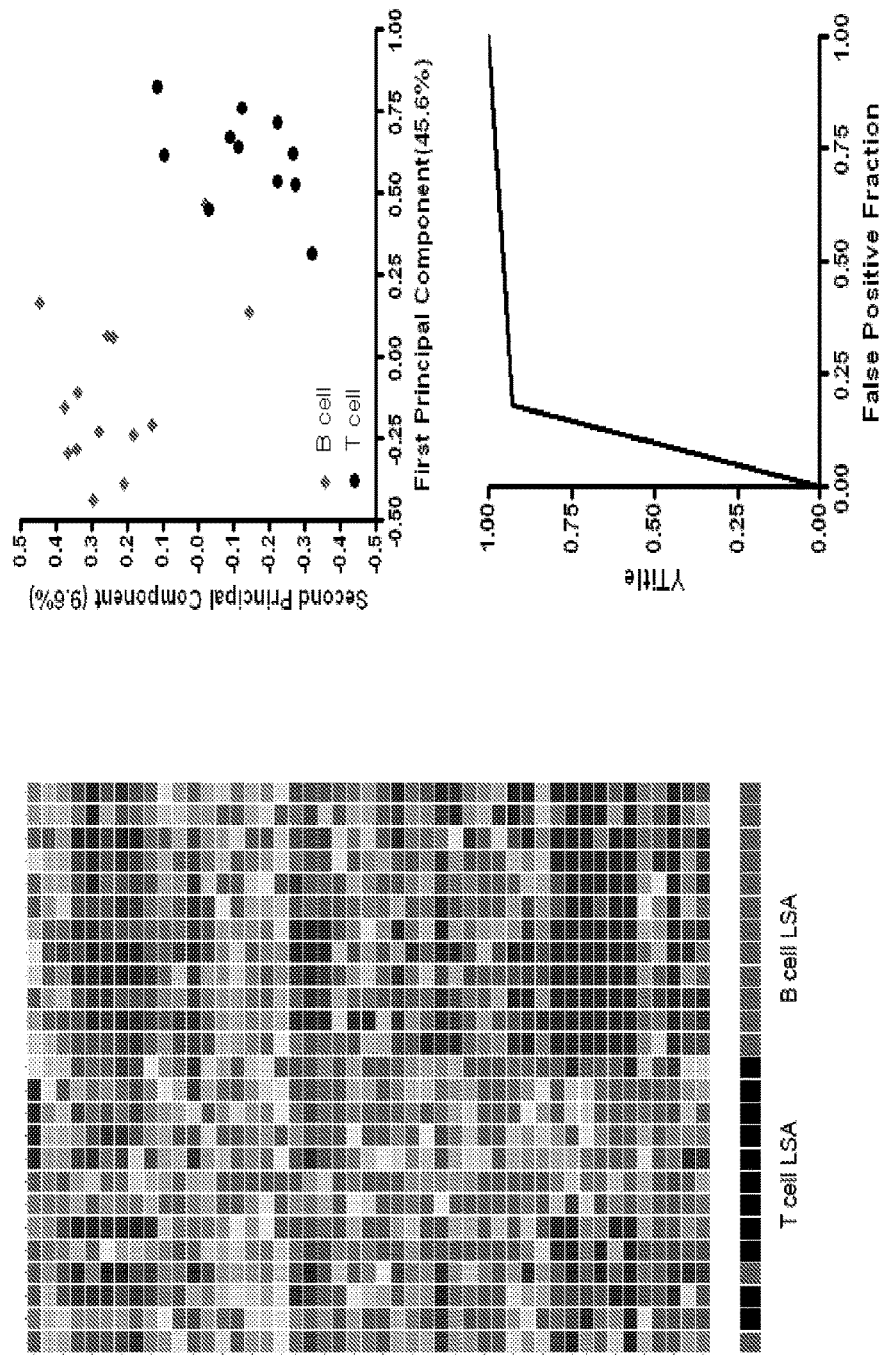
FIG. 3. The immunosignature distinguishes LSA-B from LSA-T. A Student's T-test (p<0.05 with FDR) and a 1.5 fold change between classes was used to select 47 informative peptides. The distribution of intensities is shown in the Heatmap (A). Colors represent the per peptide median normalized intensities. Yellow indicates the median, Red five fold above the median and Blue 0.25 fold below the median. Each row represents a peptide and each column represents and individual. Individuals were clustered in GeneSpring using the Pearson correlation to each other. Variation among individuals based on the 47 peptides is shown in the PCA plot (B) where the first two principal components are plotted. The classification efficacy is plotted in the ROC curve in (C). Print run one and the KPL conjugate was used for this assay.

Separation of B cell and T cell LSA is shown in the PCA in FIG. 3B. Leave one out cross validation was able to separate LSA and healthy with 88% accuracy: one member of each class was misidentified, a ROC curve is shown in FIG. 3C. Interestingly, one of the B cell patients clustering with the T cell patients and classified as a T cell patient was confirmed to have a CD3 positive lymphoma. A similar distinction was made using the CIM10Kv1 arrays (data not shown). This demonstrates that the immunosignature can distinguish lymphomas of B and T cell origin.

Characterization of the Individual Lymphoma Immunosignature. Lymphoma is a clonal disease arising from the uncontrolled proliferation of a single lymphocyte. We have observed individual immunosignatures in human myeloma, another clonal B cell disease (Stafford et al, in preparation). This raises the possibility of an immunosignature for each lymphoma patient in addition to the general class immunosignature. Such an immunosignature could be either from the antibody species produced by the B cell or the immune response to the surface markers or other cancer related antigens of the lymphoma cell. In the case of a T cell lymphoma there could be a unique antibody response to the T cell receptor of the lymphoma clone. Pattern matching analysis was done to identify peptides uniquely recognized by each dog.

Figure 4:
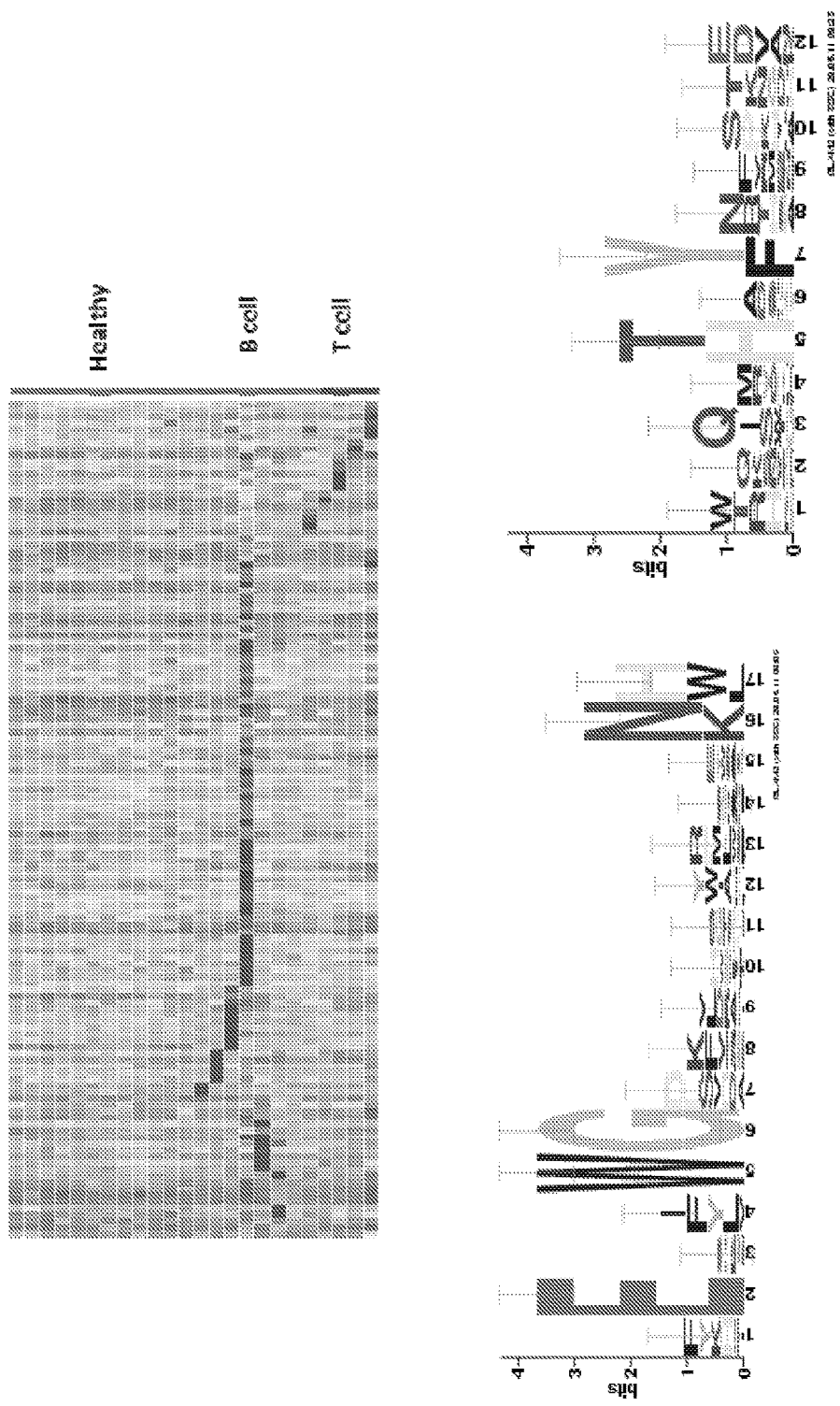
FIG. 4. Individual Lymphoma signatures. (A) Peptides comprising the unique elements of the immunosignatures of lymphoma patients are displayed in a false color heatmap. Red represents 5 fold greater than median, yellow represents the median and blue 5 fold below the median. Peptides ranked in the lowest quartile for coefficient of variation among healthy dogs were analyzed by correlation (greater than Pearson R of 0.9) to a recognition profile of 10 fold above the median in an individual and at the median for both healthy dogs and lymphoma patients. The GLAM2 pattern matching algorithm was used to establish patterns for each dog. Representative patterns for LSA-B are shown in (B & C). Print run one and the KPL conjugate was used for this assay.

To reduce the influence of recent vaccines or infections, the peptides with the least variability in healthy donors (bottom quartile ranked on CV) were analyzed. The pattern used was the per peptide median for all dogs except the LSA patient being queried for which the value was set at 5 fold above the per peptide median. Peptides matching the profile with a Pearson correlation greater than 0.90 were defined as unique to that individual. A heatmap of the unique peptides is presented in FIG. 4a. The median number of peptides identified in the B cell LSA dogs was 8 (range: 3 to 71) and the median number of identified peptides in the T cell LSA patients was 6 (range: 2 to 6). No peptides matching these profiles were bound in the healthy dogs.

If these unique peptides are bound by a single antibody clone, then a motif could be present in the peptide list. Sequence motifs were identified using the GLAM2 algorithm and representative motifs are presented as logo plots in FIGS. 4b & c. Individual immunosignatures with associated motifs were also seen on the CIM10Kv1 (not shown). Taken together, these data agree with the clonal nature of the disease and suggest that the individual immunosignature may be the result of a single antibody clone, whether that produced by the involved B cell clone or to a unique antigen such as the BCR or TCR idiotype Monitoring the Immunosignature Present at Diagnosis Marks Remission but Not Relapse. To determine if the immunosignature could be used to monitor patients for early signs of relapse, we obtained sera from 12 dogs with LSA at the time of diagnosis, 3 months following treatment at which point they were clinically in remission and at the time of relapse. The sera was run on the CIM10Kv2 and evaluated for changes both personal and subtype immunosignatures. Comparison of the individual immunosignatures between diagnosis and remission indicated that a median of 72 percent of the immunosignature decreased following initiation of treatment (Table 3). This suggests that the individual lymphoma immunosignature has utility in establishing or verifying remission.

However, the antibody reactivity level of these peptides did not return to the level observed in normal dogs. This suggests that the immune response generated against the lymphoma may be maintained by the small number of cells that lead to the recurrence. Peptides decreasing at remission did not also increase at relapse. Survival of the minimal residual disease cells and the lack of the return of decreased peptides to pretreatment levels suggests that the tumor was kept in check by the immune umbrella of the original tumor but new antigens and pathways enabled relapse.

The subtype immunosignature was defined as the peptides increased in each phenotype. For the 177 peptides increased in B cell LSA, a median of 25+/−14 peptides (14%) decreased at remission and 13+/−7 peptides increased from remission to relapse. Of the 173 peptides increased in T cell LSA, a median of 35+/−20 peptides (20%) decreased upon remission and a median of 21.4+/−6 peptides (12%) increased between remission and relapse.

Antibodies binding the subtype specific immunosignature were likely raised by a normal B cells against the LSA cell as part of the anti-lymphoma immune response. Clinical therapy either excises or chemically kills the LSA cell removing the antigen that stimulated the normal B cell. Persistence of the immunosignature after removal of the LSA cell suggests that the normal B cell had differentiated to a long lived plasma cell and was unaffected by remission. Taken together, this indicates that the immunosignature can verify remission through the personalized signature, but other means are needed to detect recurrence.

Figure 5:
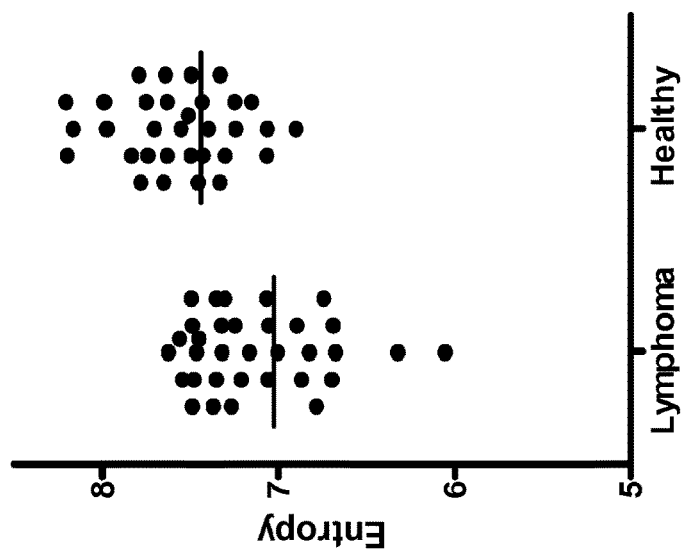
FIG. 5. Characterization of the B cell lymphoma immunosignature as (A) the dynamic range of peptides recognized and (B) the distribution as measured by entropy. Dynamic range $p=1\times10^{-4}$ Entropy p=0.019 values were calculated off the ComBat normalized values for the dynamic range and the raw values for the entropy. The dynamic range is defined as the $95^{th}$ percentile divided by the $5^{th}$ percentile. The second print batch and the Jackson conjugate were used in this assay.
Figure 5:
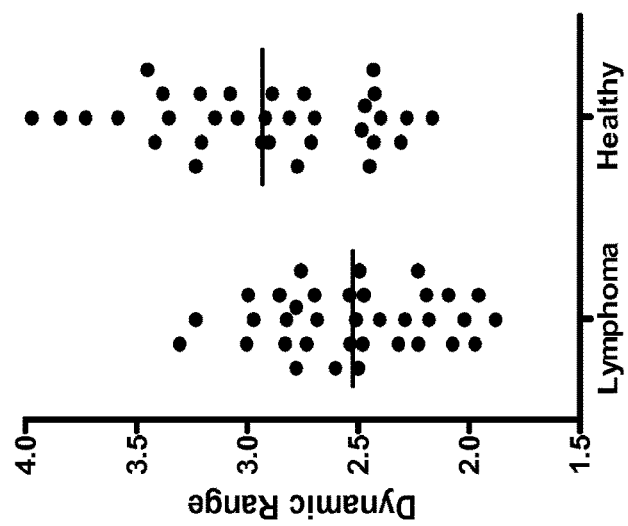

Further characterization of the B cell Lymphoma Immunosignature. Retrospective surveys of T cell LSA-T and B cell LSA identified median DFIs of 2.5 months for T cell LSA and 6.74 months for B cell LSA. In this study and in clinical practice, dogs with B cell LSA tended to have a higher proportion of survivors at later months, indicating a need to further characterize the B cell LSA immunosignature. The median raw feature intensity of arrays probed with serum from B cell LSA patients and healthy donors were compared. The median raw feature intensity of the arrays probed with B cell LSA were significantly lower ($p=1\times10^{-4}$)) than those probed with healthy donors (FIG. 5a).

In prior studies, overall feature intensity increases were noted in infection and as the concentration of antibodies applied to the array increases. This suggests that either the overall amount of immunoglobulin or reactivity is depressed in B cell LSA patients, fitting with clinical studies of non-Hodgkins lymphoma in humans, in which observed serum hypogammaglobemmia in 10 to 15% of patients and a 21% reduction of crude median IgG levels in diffuse large B-cell lymphoma patients.

Next the distribution of antibody reactivities were compared on the CIM10Kv2 array between LSA-B patients and healthy donors. Entropy measures the distribution of antibody reactivities across the intensities of features present on the array. Entropy in LSA-B patients was significantly decreased (FIG. 5b), suggesting that the circulating antibody repertoire was driven to a reduced distribution of antibody species and by extension over representation of the producing B cell clones. No correlation of either the dynamic range, median intensity or entropy was observed with the length of the disease free interval.

The Immunosignature of B cell LSA at Diagnosis is Capable of Predicting Length of Disease Free Interval in Dogs Entering Remission. Since changes in the individual or class immunosignatures following treatment were not indicative of relapse, we sought to determine if the immunosignature at diagnosis could predict time to relapse. The LSA-B patients were divided into those that relapsed in under 120 days (n=10) and those that had a delayed relapse of over 120 days (n=23). A Student's T-test identified 35 peptides with a p value <0.05 with FDR between classes.

Figure 6:
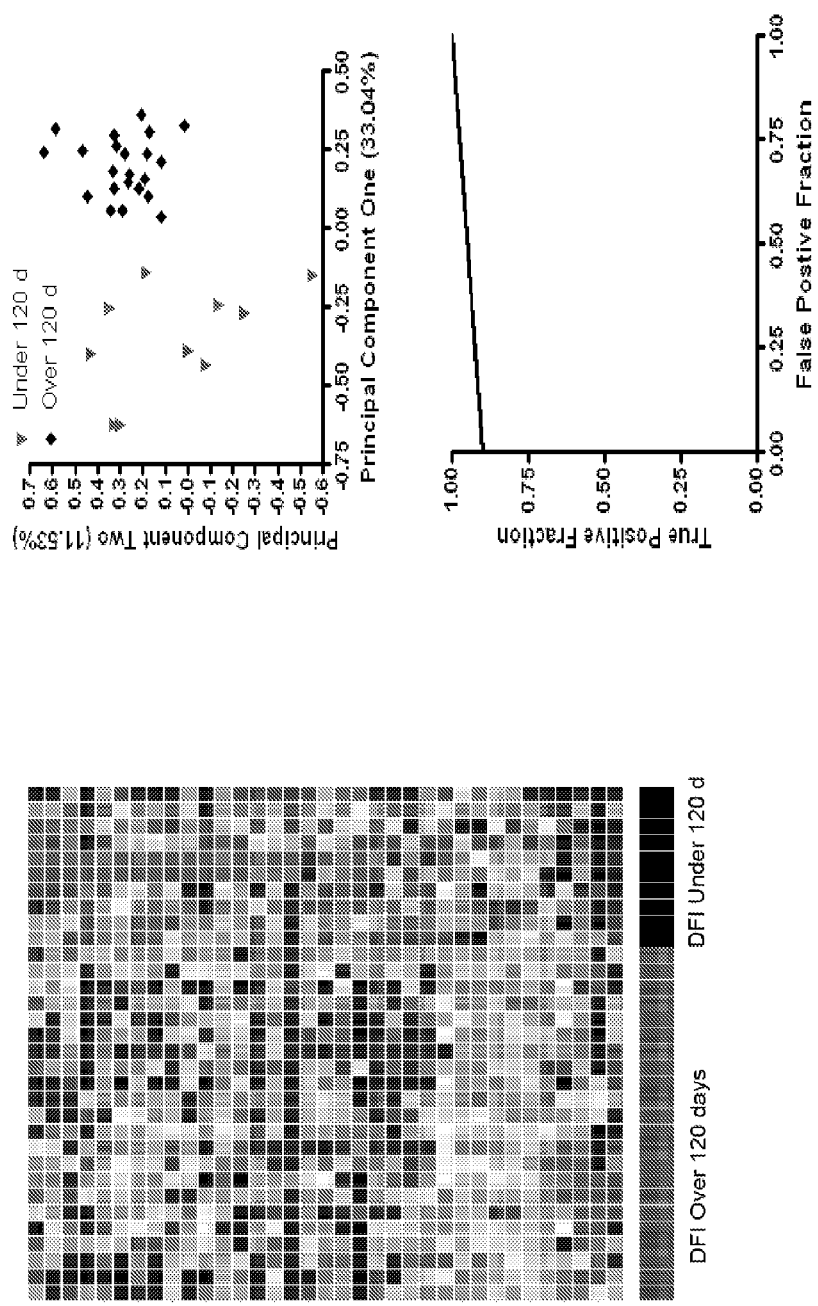
FIG. 6. The immunosignature at diagnosis can predict length of disease free interval. A Student's T-test (p<0.05 with FDR) and a 1.5 fold change between classes was used to select 35 informative peptides. The distribution of intensities is shown in the Heatmap (A). Colors represent the per peptide median normalized intensities. Yellow indicates the median, Red two fold above the median and Blue less than 0.8 fold below the median. Each row represents a peptide and each column represents and individual. Individuals were clustered in GeneSpring using distance measurement to each other. Variation among individuals based on the 35 peptides is shown in the PCA plot (B) where the first two principal components are plotted. The classification efficacy is plotted in the ROC curve in (C). Print run two and the Jackson conjugate was used for this assay.

A heatmap of the selected peptides is presented in FIG. 6a. Separation of the patients based on DFI is presented in the PCA plot shown in FIG. 6b. Note that the dogs having a longer DFI cluster more tightly than those with a short DFI having median Mahalanobis distances to the class means of 13.66 and 17.27 respectively, indicating less variance in the under 120 day immunsignature than the over 120 day immunosignature. An SVM trained on the 35 peptides has a LOOCV accuracy of 97%. A ROC curve is presented in FIG. 6c. This demonstrates that the immunosignature is capable of predicting the length of the DFI at the time of diagnosis.

Discussion. In the present study, immunosignatures have been used to characterize canine lymphoma and evaluated the immunosignature technology as a diagnostic. It has been demonstrated that lymphoma patients can be readily distinguished from healthy dogs. The immunosignature of lymphoma was capable of predicting an independent test set with high accuracy and was robust to print run and detection system changes. Furthermore, the distinction between B and T-cell lymphomas was able to be determined from the immunosignature. Individualized immunosignatures were also observed in the LSA patients at diagnosis, which declined as patients entered remission. The individualized immunosignature did not return at relapse for all dogs; however, the immunosignature at diagnosis was capable of predicting the length of the DFI. Taken together, this study demonstrates the clinical utility of the immunosignature as a multilevel diagnostic for lymphoma.

Lymphoma is a clonal disease arising from an abnormally proliferating B or T cell. Despite the clonal origin of the disease, an LSA specific immunosignature was identifiable. In humans, certain variable region genes are prevalent in lymphoma and superantigens are LSA associated, raising the possibility that the immunosignature is that of a causal immunological insult. Proteomic studies in humans have identified distinct protein expression profiles that are informative not only for LSA, but clinical subtype.

This raises the possibility that the immunosignature is reflecting cancer antigens associated with lymphoma. In individual dogs, an individual immunosignature was additionally detected and may be the product of the individual B cell clone while the class immunosignature was reflective of the underlying cancer biology. The influence of the antibody produced by the individual B cell clone is reflected in the immunosignature distinguishing LSA-B and LSA-T, where the LSA-T patients cluster together much more tightly on the PCA than do LSA-B patients.

The observation that the personalized immunosignature declined as the dog entered remission while the lymphoma class immunosignature does fit with the biology of the respective B cells. The causal B cell clone that formed the lymphoma is present in abundance at diagnosis and is excised or chemically reduced to barely detectable levels at remission, yet antibodies against the lymphoma persist. Serum IgG in dogs have a half-life of 8 to 12 days, indicating that at the three-month sampling, serum levels of the anti-LSA antibody species could have reduced to 1 to 6% of the diagnosis titer. This suggests that the anti-LSA antibody response has differentiated to long lived plasma cells which have a 140 day half-life and is largely unaffected by immunosuppressive chemotherapy.

That the personalized immunosignature did not increase upon relapse suggests that either other antigens are involved in triggering relapse of a dormant tumor cell, somatic hypermutation has occurred, or the relapse is actually a second clonal lineage initiating an antigenically distinct LSA tumor. The disease free interval in both dogs and humans is a period of watchful waiting punctuated with frequent recheck examinations, blood draws and imaging. The immunosignature at diagnosis is capable of identifying dogs having an aggressive lymphoma that relapsed in less than four months from those with a less aggressive form.

Conversion of a microarray based assay to a diagnostic is reliant on the robustness of the platform to differences in technician, print batch and detection system. In the training and test set, the sum effect of these conditions were evaluated. The training set was initially run as one batch then repeated in the second batch with the test set. When the SVM was trained using either training set batch, the test set was predicted with >94% accuracy. This demonstrates that as a practical diagnostic assay, a single patient could be normalized to a co-run standard and the immunosignature compared to a database, thereby alleviating the impractical possibility of having to run a 60 sample training set with each assay. Thus, a kit for diagnosing canine lymphoma may be provided that includes, for example, an array of immobilized peptides, a reagent for detecting a binding pattern of any antibodies to the peptides on the array, and a reference binding pattern indicative of lymphoma (e.g., access instructions to a database containing the reference pattern(s)).

These examples illustrate the immunosignature as an improvement over current veterinary serodiagnostics for lymphoma. As opposed to tests which either non-specifically indicate a cancer by measuring thymidine kinase activity or rely on biomarkers, the immunosignature is information rich. From a single assay, the patient could potentially be diagnosed as having lymphoma or not, whether the lymphoma is of B or T cell lineage and whether the DFI following chemotherapy will be short or long.

Each of these points of information is critical for the treating veterinarian. A negative immunosignature for LSA aids in the differential diagnosis, B cell LSA and T cell LSA may be treated differently, and knowing at diagnosis that the DFI will be short may provide important prognostic information to the pet owner and veterinarian. Given the similarity between both disease and immune system function in dogs and humans, the immunosignature is expected to provide the same information to physicians and their patients.

TABLE 1

Summary of Study Population Signalment.[1]

| Class | N | Age[2] | Sex[3] | | Breed |
|---|---|---|---|---|---|
| Healthy | 39 | 6 (2 to 15) | M | 24 | Mixed Breed (19), Golden Retriever (6), Labrador |
| | | | F | 15 | Retriever (3), Staffordshire Terrier (2), Australian Cattle Dog (2), Australian Shepherd, Dalmatian, Doberman, German Wire Haired Pointer, Std. Poodle, St. Bernard, Rottweiler |
| LSA-B | 38 | 7.9 (2 to 13) | M | 22 | Mixed Breed (10), Golden Retriever (5), Border Collie |
| | | | F | 16 | (4), German Shepard (2), Rottweiler (2), Scottish Terrier (2), Vizsla (2), Bassett Hound, Belgian Malinois, Boxer, Chesapeake Bay Retriever, Collie, Doberman, Labrador Retriever, Miniature Schnauzer, Sheltie, Staffordshire Terrier, Other |
| LSA-T | 11 | 6.97 (4 to 12) | M | 4 | Golden Retriever (3), Boxer (3), Mixed Breed (2), |
| | | | F | 7 | Bull Mastif, Irish Setter, Labrador Retriever |

[1]Archived serum samples from client owned dogs presenting to the Animal Cancer Center at Colorado State University were used.
[2]Median age is presented with the range, low to high, in parenthesis.
[3]Neutered and intact dogs are totaled under the appropriate sex.

TABLE 2

Summary of Iterative Classification Efficacy in Distinguishing Healthy from Lymphoma[1].

| | Peptides[2] | LOOCV Accuracy[3] | Percent Test Set Accuracy[4] | Sensitivity[5] | Specificity[6] |
|---|---|---|---|---|---|
| Median | 78 | 100% | 88.2% | 88.9% | 87.5% |
| Maximum | 98 | 100% | 100.0% | 90.0% | 100.0% |
| Minimum | 62 | 96% | 64.7% | 80.0% | 50.0% |
| Std Dev | 5 | 1% | 6.4% | 1.3% | 10.2% |

[1]The population of dogs was iteratively split into 75% training and 25% test set for 10,000 tests. Peptides were selected, an SVM trained and then used to predict the test set.
[2]The number of peptides selected using a Student's T-test (p < 0.05 with Benjamani and Hochberg multiple test correction) and a 1.5 fold change between classes.
[3]Leave one out crossvalidation accuracy where the SVM is trained on the training set minus one and used to predict the left out sample.
[4]Percent of the test set that was called correctly by the SVM trained on the training set.
[5]Percent of the true positives called correctly.
[6]Percent of the true negatives called correctly.

TABLE 3

Change in the Individual Immunosignature between Diagnosis and Reoccurrance[1].

| Individual | Type[4] | DFI (days)[5] | Peptides[6] | Portion of the Signature decreasing by 3 months[2] | | | Portion of Signature Returning to Pretreatment Levels at relapse[3] | | |
|---|---|---|---|---|---|---|---|---|---|
| | | | | Number[7] | Percent[8] | Median Fold Change At Day 90 | Number | Percent | Median Fold Change vs Day 0 |
| 247690 | B | 174 | 3 | 0 | 0 | 1.21 | 0 | 0 | 0.78 |
| 248661 | B | 280 | 5 | 1 | 20 | 0.85 | 0 | 0 | 0.59 |
| 251332 | B | 273 | 10 | 7 | 70 | 0.59 | 0 | 0 | 0.42 |
| 251661 | B | 119 | 71 | 65 | 92 | 0.42 | 5 | 7 | 0.37 |
| 252343 | B | 257 | 11 | 9 | 82 | 0.46 | 1 | 9 | 0.49 |
| 253509 | B | 270 | 7 | 7 | 100 | 0.45 | 0 | 0 | 0.20 |
| 256744 | B | 112 | 3 | 1 | 33 | 0.87 | 1 | 33 | 0.94 |
| 257195 | B | 333 | 4 | 3 | 75 | 0.69 | 1 | 25 | 0.45 |
| 219623 | T | 185 | 2 | 1 | 50 | 0.78 | 1 | 50 | 0.95 |
| 238300 | T | 167 | 5 | 4 | 80 | 0.54 | 0 | 0 | 0.49 |

TABLE 3-continued

Change in the Individual Immunosignature between Diagnosis and Reoccurrance[1].

| Individual | Type[4] | DFI (days)[5] | Peptides[6] | Portion of the Signature decreasing by 3 months[2] | | | Portion of Signature Returning to Pretreatment Levels at relapse[3] | | |
|---|---|---|---|---|---|---|---|---|---|
| | | | | Number[7] | Percent[8] | Median Fold Change At Day 90 | Number | Percent | Median Fold Change vs Day 0 |
| 243388 | T | 270 | 3 | 3 | 100 | 0.37 | 3 | 100 | 1.42 |
| 251702 | T | 71 | 6 | 0 | 0 | 1.37 | 0 | 0 | 1.40 |

[1]The individual signature is defined as the number of peptides uniquely recognized by each individual compared to other dogs in the study.
[2]The number of peptides in the individual immunosignature that decreased in normalized RFI greater than the minimum detectable fold change of 0.76.
[3]The number of peptides with a normalized RFI that returned to within the minimum detectable fold change of 0.76 to 1.3x of the values at diagnosis by the time they were clinically out of remission.
[4]Phenotype of the lymphoma, B cell or T cell.
[5]Time between initiation of treatment and being clinically defined as out of remission.
[6]The number of peptides comprising the individual immunsignature.
[7]The number of peptides comprising the individual immunsignature that decreased at three months.
[8]Percent of the individual immunosignature that decreased at three months

REFERENCES

1. Siegel R, Naishadham D, Jemal A. Cancer statistics, 2013. CA Cancer J Clin 2013; 63(1):11-30.
2. Shankland K R, Armitage J O, Hancock B W. Non-Hodgkin lymphoma. Lancet 2012; 380(9844):848-57.
3. Evans L S, Hancock B W. Non-Hodgkin lymphoma. Lancet 2003; 362(9378):139-46.
4. Larouche J F, Berger F, Chassagne-Clement C, et al. Lymphoma recurrence 5 years or later following diffuse large B-cell lymphoma: clinical characteristics and outcome. J Clin Oncol 2010; 28(12):2094-100.
5. Marconato L, Gelain M E, Comazzi S. The dog as a possible animal model for human non-Hodgkin lymphoma: a review. Hematol Oncol 2013; 31(1):1-9.
6. Vail D M, Young K M. Hematopoietic tumors. In: WIthrow S J, Vail D M, editors. Small Animal Clinical Oncology. 4th ed. St. Louis: Saunders Elsevier; 2007. p. 699-784.

The disclosure described above is not intended to be limited to the embodiments and examples described herein.

What is claimed is:

1. A method for detecting canine lymphoma, using a machine readable random peptide array, through binding of peptides on said array with an antibody-containing sample derived from a canine, and treating canine lymphoma, comprising the steps of:
   contacting the antibody-containing sample from said canine with a predetermined array of immobilized peptides,
   detecting a pattern of binding indicative of canine lymphoma of the sample to the peptides on the array with a scanner; and
   treating a canine with detected lymphoma with chemotherapy.

2. The method of claim 1, wherein said steps are performed to detect a binding pattern indicative of remission following chemotherapy.

3. The method of claim 1, wherein said steps are performed to detect a binding pattern indicative of recurrence following chemotherapy.

4. A method for distinguishing canine B-cell lymphoma from T-cell lymphoma, using a machine readable random peptide array, through binding of peptides on said array with an antibody-containing sample derived from a canine, and treating canine lymphoma, comprising the steps of:
   contacting the antibody-containing sample from said canine with a predetermined array of immobilized peptides,
   detecting a pattern of binding indicative of canine B cell or T cell lymphoma of the sample to the peptides on the array with a scanner; and
   treating a canine with a B cell- or T cell-specific lymphoma chemotherapy.

5. The method of claim 1, wherein detecting the pattern of binding indicative of canine lymphoma of the sample to the peptides on the array with said scanner comprises aligning raw array images with said scanner and statistical processing of said images with a computer.

6. The method of claim 1, wherein said pattern of binding indicative of canine lymphoma comprises 340 peptides.

* * * * *